Figure 1:
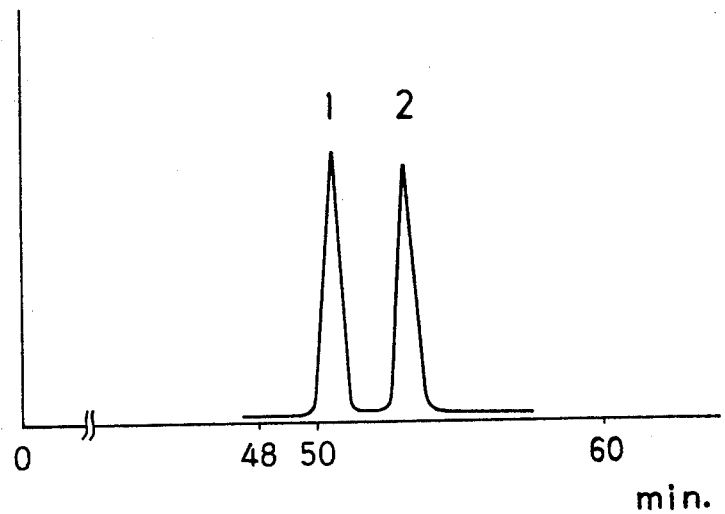

United States Patent [19]

Oi et al.

[11] 4,104,040
[45] Aug. 1, 1978

[54] USE OF S-TRIAZINE DERIVATIVES IN A GAS CHROMATOGRAPHIC METHOD

[75] Inventors: Naobumi Oi; Koichi Moriguchi, both of Kyoto; Mari Matsuda, Ibaraki, all of Japan

[73] Assignee: Sumitomo Chemical Company, Limited, Japan

[21] Appl. No.: 760,849

[22] Filed: Jan. 21, 1977

Related U.S. Application Data

[62] Division of Ser. No. 660,680, Feb. 23, 1976, abandoned.

[51] Int. Cl.$^2$ ............................................. B01D 15/08
[52] U.S. Cl. ......................................... 55/67; 55/386; 23/232 C
[58] Field of Search ............................ 55/67, 386, 74; 210/198 C; 23/232 C

[56] References Cited

U.S. PATENT DOCUMENTS 3,666,792  5/1972  Langea ................................. 55/67 X

OTHER PUBLICATIONS

Chromatography Abstracts 1958-1972 by Knarman et al., The Institute of Metaoleum-London.

*Primary Examiner*—John Adee
*Attorney, Agent, or Firm*—Birch, Stewart, Kolasch and Birch

[57] ABSTRACT

An s-triazine derivative with at least one asymmetric carbon atom of the general formula:

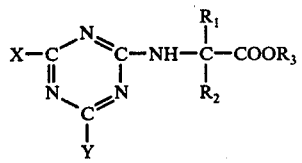

wherein $R_1$ and $R_2$ are different and are each hydrogen, an alkyl, an aralkyl or phenyl; $R_3$ is an alkyl, a cycloalkyl, an aralkyl or phenyl; and X and Y are the same or different:

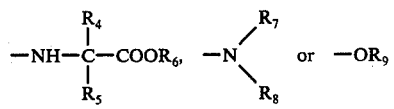

wherein $R_4$, $R_5$, $R_7$, $R_8$ and $R_9$ are the same or different and are each hydrogen, an alkyl, a cycloalkyl, an aralkyl or phenyl; and $R_6$ is an alkyl, a cycloalkyl, an aralkyl or phenyl, and a gas chromatographic method for the resolution and analysis of the mixture of enantiomers having an —NH— group linked to an asymmetric carbon atom, or to an atom in α-position with respect to an asymmetric carbon atom, comprising using said derivative as an optically active stationary phase for the gas chromatography.

11 Claims, 3 Drawing Figures

USE OF S-TRIAZINE DERIVATIVES IN A GAS CHROMATOGRAPHIC METHOD

This application is a divisional of copending application Ser. No. 660,680, filed on Feb. 23, 1976, now abandoned.

The present invention relates to a gas chromatographic method for the resolution and analysis of the mixture of enantiomers having an —NH— group linked to an asymmetric carbon atom or to an atom in α-position with respect to an asymmetric carbon atom, using an s-triazine derivative with at least one asymmetric carbon atom as an optically active stationary phase for the gas chromatography.

Hitherto, for the gas chromatographic resolution and analysis of a mixture of enantiomers having the —NH— group as mentioned above, there has widely been used a method which comprises reacting said mixture with a suitable optically active reagent to form the diastereomers and then resolving and analyzing the diastereomers by gas chromatography on the usual optically inactive stationary phase. However, this method has the following defects: (1) the optical purity of optically active reagents used for the formation of diastereomers gives a direct effect on the analytical value; (2) the rate of the formation of diastereomers is sometimes different between the enantiomers; and (3) the formation of diastereomers is sometimes accompanied with optical isomerization. Therefore, the direct resolution and analysis of the mixture of enantiomers by gas chromatography on an optically active stationary phase, not passing through the formation of diastereomers, has strongly been required.

As the optically active stationary phase for gas chromatography which can achieve such an object and which are now in the practical use, there are only three groups consisting of N-acylated polypeptide esters, carbonyl-bis-amino acid esters and amino acid amides (U.S. Pat. No. 3,494,105). These compounds have a large value. However, in the direct resolution and analysis of the mixture of enantiomers by gas chromatography on an optically active stationary phase, the mixture of enantiomers must be passed through the column with attention so that the enantiomers per se are not optically isomerized by heat. It is therefore desirable to keep the column temperature as low as possible. On the other hand, when the enantiomers are hardly optically isomerized, it is desirable to keep the column temperature as high as possible in order to enable the resolution and analysis of compounds having a high boiling point additionally. The known three compound groups as mentioned above are disadvantageous in this respect, because they have a relatively high melting point or poor heat resistance so that they are only applicable to a narrow range of analysis. It is of course possible to carry out the analysis at the column temperature of lower than the melting point of the stationary phase. In this case, however, the state of the stationary phase becomes solid or nematic, resulting in a reduction of theoretical plates and as the result the peaks obtained become broad or abnormal in phase. Therefore it becomes difficult to resolve and analyze a mixture of many kinds of enantiomers.

It is an object of the present invention to provide an improved and excellent stationary phase which can be used as a liquid phase at a relatively low column temperature, preferably even lower than 100° C, has a high resistance to heat, and which gives, over a wide range of column temperature, a sharp and highly symmetric peak which is suitable for analysis.

Another object of the invention is to provide a novel s-triazine derivative with at least one asymmetric carbon atom useful as the optically active stationary phase for the gas chromatographic resolution and analysis of a mixture of enantiomers having an —NH— group linked to an asymmetric carbon atom or to an atom in α-position with respect to an asymmetric carbon atom.

A further object of the invention is to provide a gas chromatographic method for the resolution and analysis of said mixture of enantiomers by using the s-triazine derivative as set forth above.

These and other objects of the invention will be apparent from the description hereinafter.

The optically active stationary phase according to the present invention is an s-triazine derivative with at least one asymmetric carbon atom of the general formula:

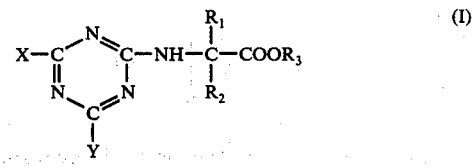

wherein $R_1$ and $R_2$ are different and are each hydrogen, an alkyl having 1 to 8 carbon atoms, an aralkyl having 1 to 2 carbon atoms in the alkyl moiety or phenyl; $R_3$ is an alkyl having 1 to 12 carbon atoms, a cycloalkyl having 5 to 6 carbon atoms, an aralkyl having 1 to 2 carbon atoms in the alkyl moiety or phenyl; and X and Y are the same or different and are each a member selected from the group consisting of the groups:

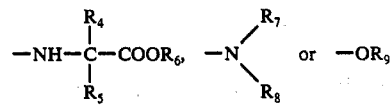

wherein $R_4$, $R_5$, $R_7$, $R_8$ and $R_9$ are the same or different and are each hydrogen, an alkyl having 1 to 8 carbon atoms, a cycloalkyl having 5 to 6 carbon atoms, an aralkyl having 1 to 2 carbon atoms in the alkyl moiety or phenyl; and $R_6$ is an alkyl having 1 to 12 carbon atoms, a cycloalkyl having 5 to 6 carbon atoms, an aralkyl having 1 to 2 carbon atoms in the alkyl moiety or phenyl. For example, 2,4bis-(1-carboisopropoxy-2-methyl-l-1-propylamino)-6-ethoxy-s-triazine is a viscous liquid substance in the vicinity of room temperature and it is used as a liquid phase even at a column temperature of lower than 100° C. This compound is very suitable for the resolution and analysis of a mixture of enantiomers having an —NH— group linked to an asymmetric carbon atom, for example, N-trifluoroacetyl-dl-alanine t-butyl ester, because the peaks are well separable and have a sharp and highly symmetric shape. Further, 2,4,6-tris(1-carboisopropoxy-2-methyl-l-1-propylamino)-s-triazine is a viscous liquid substance in the vicinity of room temperature and is superior in its heat resistance so that it can stably be used even at 150° C. The compound is characterized by applicability to the gas chromatographic resolution and analysis of a mixture of enantiomers having a high boiling point, for example, N-pentafluoropropionyl-dl-α-naphthylethylamine.

In the present specification, the term "alkyl" denotes a straight or branched alkyl having 1 to 12 carbon atoms, such as methyl, ethyl, propyl, isopropyl, butyl, isobutyl, sec-butyl, tert-butyl, pentyl, hexyl, heptyl, octyl, decyl, undecyl or dodecyl; "cycloalkyl" denotes a cycloalkyl having 5 to 6 carbon atoms, such as cyclopentyl or cyclohexyl; and "aralkyl" denotes an arylalkyl having 1 or 2 carbon atoms in the alkyl moiety, such as benzyl or phenethyl.

In the preferred embodiment of the s-triazine derivative of the formula (I), $R_1$ and $R_2$ are different and are each hydrogen, a straight or branched alkyl having 1 to 4 carbon atoms, more preferably 1 to 3 carbon atoms, or benzyl; $R_3$ is a straight or branched alkyl having 1 to 12 carbon atoms, more preferably 1 to 3 carbon atoms, or cycloalkyl having 5 to 6 carbon atoms, more preferably cyclohexyl; and X and Y are the same or different and are each the group:

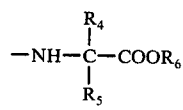

wherein $R_4$ and $R_5$ are the same or different and are each hydrogen, a straight or branched alkyl having 1 to 4 carbon atoms, more preferably 1 to 3 carbon atoms, or benzyl, and $R_6$ is a straight or branched alkyl having 1 to 12 carbon atoms, more preferably 1 to 3 carbon atoms, or a cycloalkyl having 5 to 6 carbon atoms, more preferably cyclohexyl; or the group:

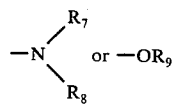

wherein $R_7$, $R_8$ and $R_9$ are the same or different and are each hydrogen, a straight or branched alkyl having 1 to 12 carbon atoms, more preferably 2 to 8 carbon atoms, or cycloalkyl having 5 to 6 carbon atoms, more preferably cyclohexyl.

Particularly suitable s-triazine derivatives with at least one asymmetric carbon atom are represented by the following formulae:

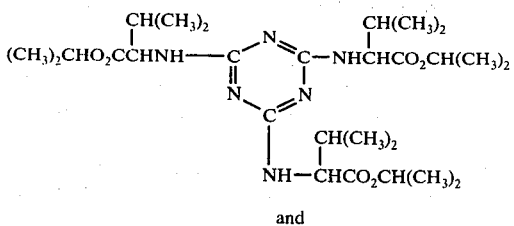

and

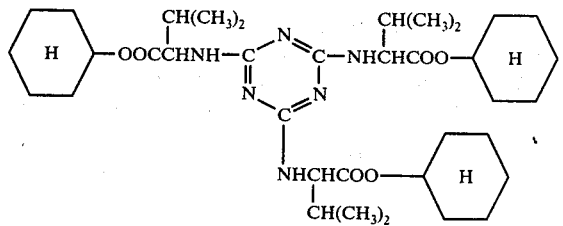

The s-triazine derivatives of the general formula (I) according to the present invention can be prepared by the well-known methods disclosed, for example, in Journal of the American Pharmaceutical Association, Vol. XIL, No. 7, 461 – 463, which comprises reacting an amino acid ester with cyanuric chloride in an inert solvent in the presence of an acid-binding agent such as sodium carbonate or potassium carbonate and, if necessary, reacting the resulting s-triazine substituted with one or two members selected from amino acid esters with an alcohol, amines or mercaptans.

Examples of the compound according to the present invention are shown in Table 1 with the following general formula:

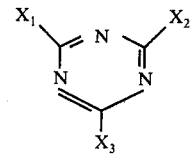

Table 1

| No. | Compound | $X_1$ | $X_2$ | $X_3$ | Elementary analysis Calcd. | Elementary analysis Found | Optical rotation |
|---|---|---|---|---|---|---|---|
| 1 | 2-(1-Carboisopropoxy-2-methyl-1-1-propylamino)-4,6-bisethoxy-s-triazine | CH(CH$_3$)$_2$—NHCHCOOCH(CH$_3$)$_2$ | OC$_2$H$_5$ | OC$_2$H$_5$ | C 55.2<br>H 8.0<br>N 17.2 | C 55.0<br>H 7.7<br>N 17.2 | $[\alpha]_{546}^{22} -11.9°$<br>(c, 0.64, CHCl$_3$) |
| 2 | 2-(1-carboisopropoxy-2-methyl-1-1-propylamino)-4,6-biscyclohexylamino-s-triazine | CH(CH$_3$)$_2$—NHCHCOOCH(CH$_3$)$_2$ | ⬡—NH— | ⬡—NH— | C 64.9<br>H 7.8<br>N 19.8 | C 63.7<br>H 7.5<br>N 19.4 | $[\alpha]_D^{22} -16.6°$<br>(c, 0.7, CHCl$_3$) |
| 3 | 2,4-Bis(1-carboisopropoxy-2-methyl-1-1-propylamino)-6-ethoxy-s-triazine | CH(CH$_3$)$_2$—NHCHCOOCH(CH$_3$)$_2$ | CH(CH$_3$)$_2$—NHCHCOOCH(CH$_3$)$_2$ | OC$_2$H$_5$ | C 57.4<br>H 8.4<br>N 16.0 | C 57.8<br>H 8.7<br>N 15.8 | $[\alpha]_D^{22} -33.1°$<br>(c, 3.7, CHCl$_3$) |
| 4 | 3,4-Bis(1-carboisopropoxy-2-methyl-1-1-propylamino)-6-octylamino-s-triazine | CH(CH$_3$)$_2$—NHCHCOOCH(CH$_3$)$_2$ | CH(CH$_3$)$_2$—NHCHCOOCH(CH$_3$)$_2$ | NHC$_8$H$_{17}$ | C 62.1<br>H 9.6<br>N 16.1 | C 62.6<br>H 10.2<br>N 15.5 | $[\alpha]_{546}^{22} -35.1°$<br>(c, 0.33, CHCl$_3$) |
| 5 | 2,4-Bis(1-carboisopropoxy-2-methyl-1-1-propylamino)-6-cyclohexylamino-s-triazine | CH(CH$_3$)$_2$—NHCHCOOCH(CH$_3$)$_2$ | CH(CH$_3$)$_2$—NHCHCOOCH(CH$_3$)$_2$ | ⬡—NH— | C 61.1<br>H 8.8<br>N 17.1 | C 60.5<br>H 9.5<br>N 17.3 | $[\alpha]_D^{22} -52.8°$<br>(c, 3.7, CHCl$_3$) |
| 6 | 2,4,6-Tris(1-carboisopropoxy-2-methyl-1-1-propylamino)-s-triazine | CH(CH$_3$)$_2$—NHCHCOOCH(CH$_3$)$_2$ | CH(CH$_3$)$_2$—NHCHCOOCH(CH$_3$)$_2$ | CH(CH$_3$)$_2$—NHCHCOOCH(CH$_3$)$_2$ | C 58.7<br>H 8.7<br>N 15.2 | C 58.1<br>H 9.0<br>N 15.0 | $[\alpha]_D^{22} -35.3°$<br>(c, 0.11, CHCl$_3$) |
| 7 | 2,4,6-Tris(1-carbocyclohexyloxy-2-methyl-1-1-propylamino)-s-triazine | CH(CH$_3$)$_2$—NHCHCOO—⬡ | CH(CH$_3$)$_2$—NHCHCOO—⬡ | CH(CH$_3$)$_2$—NHCHCOO—⬡ | C 64.3<br>H 8.9<br>N 12.5 | C 64.2<br>H 9.1<br>N 12.7 | $[\alpha]_{546}^{22} -57.4°$<br>(c, 1.1, CHCl$_3$) |
| 8 | 2,4,6-Tris(1-carbomethoxy-1-1-ethylamino)-s-triazine | CH$_3$—NHCHCOOCH$_3$ | CH$_3$—NHCHCOOCH$_3$ | CH$_3$—NHCHCOOCH$_3$ | C 46.9<br>H 6.3<br>N 21.9 | C 46.0<br>H 6.8<br>N 21.9 | $[\alpha]_{546}^{22} -11.7°$<br>(c, 0.36, CHCl$_3$) |
| 9 | 2,4,6-Tris(1-carboisopropoxy-1-1-ethylamino)-s-triazine | CH$_3$—NHCHCOOCH(CH$_3$)$_2$ | CH$_3$—NHCHCOOCH(CH$_3$)$_2$ | CH$_3$—NHCHCOOCH(CH$_3$)$_2$ | C 53.9<br>H 7.7<br>N 18.0 | C 53.7<br>H 8.0<br>N 18.2 | $[\alpha]_{546}^{22} -43.2°$<br>(c, 0.46, CHCl$_3$) |
| 10 | 2,4,6-Tris(1-carbomethoxy-2-methyl-1-1-propylamino)-s-triazine | CH(CH$_3$)$_2$—NHCHCOOCH$_3$ | CH(CH$_3$)$_2$—NHCHCOOCH$_3$ | CH(CH$_3$)$_2$—NHCHCOOCH$_3$ | C 53.9<br>H 7.7<br>N 18.0 | C 53.5<br>H 8.0<br>N 17.9 | $[\alpha]_{546}^{22} -81.2°$<br>(c, 1.33, CHCl$_3$) |
| 11 | The compound corresponding to No. 6 which is prepared using three d-amino acids | d- CH(CH$_3$)$_2$—NHCHCOOCH(CH$_3$)$_2$ | d- CH(CH$_3$)$_2$—NHCHCOOCH(CH$_3$)$_2$ | d- CH(CH$_3$)$_2$—NHCHCOOCH(CH$_3$)$_2$ | C 58.7<br>H 8.7<br>N 15.2 | C 58.4<br>H 9.1<br>N 14.8 | $[\alpha]_{546}^{22} +94.3°$<br>(c, 5.7, CHCl$_3$) |
| 12 | The compound corresponding to No. 6 which is prepared using two d-amino acid and one l-amino acid | d- CH(CH$_3$)$_2$—NHCHCOOCH(CH$_3$)$_2$ | d- CH(CH$_3$)$_2$—NHCHCOOCH(CH$_3$)$_2$ | l- CH(CH$_3$)$_2$—NHCHCOOCH(CH$_3$)$_2$ | C 58.7<br>H 8.7<br>N 15.2 | C 58.8<br>H 9.5<br>N 15.1 | $[\alpha]_{546}^{22} +33.1°$<br>(c, 5.2, CHCl$_3$) |

For the application of the optically active stationary phase according to the present invention to the gas chromatographic resolution and analysis, the conventional methods, for example, the packed column system which uses a column packed with the stationary phase supported on stationary phase supports, or the capillary column system which uses a column having its inner surface coated with the stationary phase alone, can be utilized. The optically active stationary phase according to the present invention can be applied both to the analysis and preparation of a mixture of enantiomers having an —NH— group linked to an asymmetric carbon atom or to an atom in α-position with respect to an asymmetric carbon atom. For the analytical purpose, the capillary column system is preferred in general, while for the preparative purpose the packed column system is suitable.

The present invention will be illustrated with reference to FIGS. 1-3 and the following examples, which are only given for the purpose of illustration and are not to be interpreted as limiting the invention thereto.

EXAMPLE 1

One hundred and twenty-five ml (1.64 mole) of isopropanol was cooled to −10° C with a freezing mixture of dry ice-methanol, and 30 ml (0.42 mole) of thionyl chloride was added dropwise thereto while stirring. Thereafter, 25 g (0.21 mole) of l-valine was added little by little while maintaining this temperature. The reaction mixture was first raised to room temperature gradually and then finally it was reacted at 100° C for 40 hours while stirring. After completion of the reaction, unreacted thionyl chloride and isopropanol were evaporated in vacuo. The residue obtained was dissolved in 10 to 20 ml of water. The solution was covered with 400 ml of ether and an aqueous ammonia was added thereto until the phenolphthalein indicator turned red. After extracting the solution with ether three to four times, the ether extract was dried over anhydrous sodium sulfate and distilled under reduced pressure to obtain a colorless and clear l-valine isopropyl ester (B.P. 40° − 41° C/3 − 4 mmHg).

Ten and one fifth grams (0.055 mole) of cyanuric chloride was dissolved in 200 ml of acetone and to the resulting solution was added dropwise at 0° C a solution of 17.4 g of the l-valine isopropyl ester in 40 ml of acetone. After the dropwise addition had been completed, the reaction mixture was raised to room temperature and 5.8 g (0.055 mole) of anhydrous sodium carbonate was added thereto. The mixture was reacted at 40° to 50° C for 10 hours. After completion of the reaction, the white precipitates were filtered off and the acetone was evaporated in vacuo to obtain 2,4-bis(1-carboisopropoxy-2-methyl-l-1-propylamino)-6-chloro-s-triazine as a white solid material. The product was added to excess ethanol and the mixture was stirred under reflux for 10 hours in the presence of an equivalent amount of anhydrous sodium carbonate, followed by ether extraction and active carbon treatment. Thus, 2,4-bis(1-carboisopropoxy-2-methyl-l-1-propylamino)-6-ethoxy-s-triazine was obtained. The elementary analysis and optical rotation were as follows: N % = 15.81 (calcd., 15.95); $[\alpha]_D^{22}$ −33.1° (C, 3.73, CHCl$_3$).

The compound thus obtained was coated on the inner surface of the glass capillary column of 0.25 mm in internal diameter and 30 m in length and N-trifluoroacetyl-dl-alanine t-butyl ester analyzed under the following test conditions to obtain the as chromatogram as shown in FIG. 1:

| Column temperature: | 95° C |
|---|---|
| Detector: | FID |
| Inlet temperature: | 200° C |
| Carrier gas: | He |
| Flow rate: | 3.3 ml/min |
| Split ratio: | 1 : 31 |

In said gas chromatogram, the peak 1 corresponds to N-trifluoroacetyl-d-alanine t-butyl ester and the peak 2 corresponds to N-trifluoroacetyl-l-alanine t-butyl ester.

The time required for all the l-enantiomers to emerge from the column was about 55 minutes.

EXAMPLE 2

2,4-Bis-(1-carboisopropoxy-2-methyl-l-1-propylamino)-6-chloro-s-triazine obtained in the same manner as in Example 1 was added to excess cyclohexylamine and the mixture was stirred under reflux for 10 hours in the presence of an equivalent amount of anhydrous sodium carbonate, followed by ether extraction and active carbon treatment. Thus, 2,4-bis(1-carboisopropoxy-2-methyl-l-1-propylamino)-6-cyclohexylamino-s-triazine was obtained. The elementary analysis and optical rotation were as follows: N % = 17.27 (calcd., 17.28); $[\alpha]_D^{22}$ −52.8° (C, 3.74, CHCl$_3$).

Figure 2:
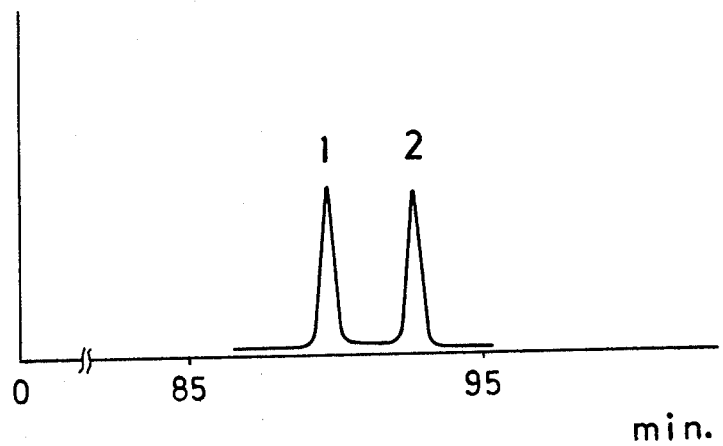

The compound thus obtained was coated on the inner surface of the capillary column of 0.25 mm in internal diameter and 34 m in length and N-trifluoroacetyl-dl-α-phenethylamine was analyzed under the following test conditions to obtain the gas chromatogram as shown in FIG. 2:

| Column temperature: | 95° C |
|---|---|
| Detector: | FID |
| Inlet temperature: | 200° C |
| Carrier gas: | He |
| Flow rate: | 3.8 ml/min |
| Split ratio: | 1 : 31 |

In said gas chromatogram, the peaks 1 and 2 correspond to N-trifluoroacetyl-d-α-phenethylamine and N-trifluoroacetyl-l-α-phenethylamine, respectively.

The time required for all the l-enantiomers to emerge from the column was about 94 minutes.

EXAMPLE 3

2,4-Bis(1-carboisopropoxy-2-methyl-l-1-propylamino)-6-chloro-s-triazine obtained in the same manner as in Example 1 was added to excess l-valine isopropyl ester and the mixture was stirred under reflux for 10 hours in the presence of an equivalent amount of anhydrous sodium carbonate, followed by ether extraction and active carbon treatment. Thus, 2,4,6-tris(1-carboisopropoxy-2-methyl-l-1-propylamino)-s-triazine was obtained. The elementary analysis and optical rotation were as follows: N % = 10.9 (calcd., 10.7); $[\alpha]_D^{22}$ −35.3° (c, 0.113, CHCl$_3$).

Figure 3:
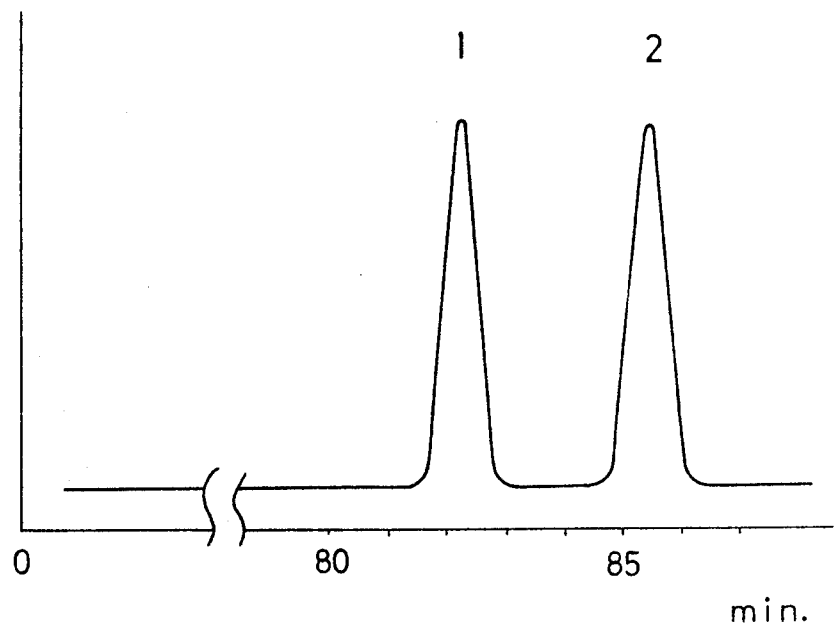

The compound thus obtained was coated on the inner surface of the glass capillary column of 0.25 mm in internal diameter and 30 m in length and N-pentafluoropropionyl-dl-α-naphthylethylamine was analyzed under the following test conditions to obtain the gas chromatogram as shown in FIG. 3:

| Column temperature: | 150° C |
|---|---|

| | |
|---|---|
| Detector: | FID |
| Inlet Temperature: | 200° C |
| Carrier gas: | He |
| Flow rate: | 1.3 ml/min |
| Split ratio: | 1 : 88 |

In said gas chromatogram, the peak 1 corresponds to N-pentafluoropropionyl-d-α-naphthylethylamine and the peak 2 corresponds to N-pentafluoropropionyl-l-α-naphthylethylamine.

The time required for all the l-enantiomer to emerge from the column was about 85.5 minutes.

What is claimed is:

1. In a gas chromatographic method for the resolution and analysis of a mixture of enantiomers having an —NH— group linked to an asymmetric carbon atom or to an atom in the α-position with respect to an asymmetric carbon atom comprising reacting said mixture with an optically active reagent to form the diastereomers and resolving and analyzing the diastereomers on an optically inactive stationary phase, the improvement which comprises using as the stationary phase an s-triazine derivative with at least one asymmetric carbon atom of the following general formula:

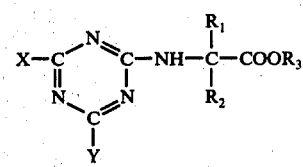

wherein $R_1$ and $R_2$ are different and are each hydrogen, an alkyl having 1 to 8 carbon atoms, an aralkyl having 1 to 2 carbon atoms in the alkyl moiety or phenyl; $R_3$ is an alkyl having 1 to 12 carbon atoms, a cycloalkyl having 5 to 6 carbon atoms, an aralkyl having 1 to 2 carbon atoms in the alkyl moiety or phenyl; and X and Y are the same or different and are each a member selected from the group consisting of the moieties:

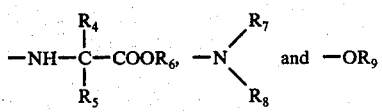

wherein $R_4$, $R_5$, $R_7$, $R_8$ and $R_9$ are the same or different and are each hydrogen, an alkyl having 1 to 8 carbon atoms, a cycloalkyl having 5 to 6 carbon atoms, an aralkyl having 1 to 2 carbon atoms in the alkyl moiety or phenyl; and $R_6$ is an alkyl having 1 to 12 carbon atoms, a cycloalkyl having 5 to 6 carbon atoms, an aralkyl having 1 to 2 carbon atoms in the alkyl moiety or phenyl.

2. The method according to claim 1, wherein $R_1$, $R_2$, $R_4$, $R_5$, $R_7$, $R_8$ and $R_9$ are the same or different and are each hydrogen, an alkyl having 1 to 8 carbon atoms or cyclohexyl, with the proviso that $R_1$ and $R_2$ is different; and $R_3$ and $R_6$ are the same or different and are each an alkyl having 1 to 3 carbon atoms or cyclohexyl.

3. The method according to claim 1, wherein $R_1$ and $R_2$ are different and are each hydrogen, a straight or branched alkyl having 1 to 4 carbon atoms or benzyl; $R_3$ is a straight or branched alkyl having 1 to 12 carbon atoms or a cycloalkyl having 5 to 6 carbon atoms; and X and Y are the same or different and are each the group:

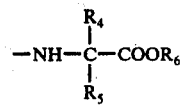

wherein $R_4$ and $R_5$ are the same or different and are each hydrogen, a straight or branched alkyl having 1 to 4 carbon atoms or benzyl, and $R_6$ is a straight or branched alkyl having 1 to 12 carbon atoms or a cycloalkyl having 5 to 6 carbon atoms; or the group:

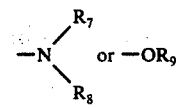

wherein $R_7$, $R_8$ and $R_9$ are the same or different and are each hydrogen, a straight or branched alkyl having 1 to 12 carbon atoms or cycloalkyl having 5 to 6 carbon atoms.

4. The method according to claim 1, wherein $R_1$ and $R_2$ are different and are each hydrogen or straight or branched alkyl having 1 to 3 carbon atoms; $R_3$ and $R_6$ are the same or different and are each a straight or branched alkyl having 1 to 3 carbon atoms or cyclohexyl; $R_4$ and $R_5$ are the same or different and are each hydrogen or a straight or branched alkyl having 1 to 3 carbon atoms; and $R_7$, $R_8$ and $R_9$ are the same or different and are each hydrogen, a straight or branched alkyl having 2 to 8 carbon atoms or cyclohexyl.

5. The method according to claim 1, wherein $R_1$ and $R_2$ are different and are each hydrogen, a straight or branched alkyl having 1 to 4 carbon atoms or benzyl; $R_3$ is a straight or branched alkyl having 1 to 8 carbon atoms or cyclohexyl; and X and Y are the same or different and are each the group:

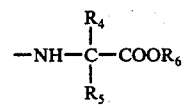

wherein $R_4$ and $R_5$ are the same or different and are each hydrogen, a straight or branched alkyl having 1 to 4 carbon atoms or benzyl and $R_6$ is a straight or branched alkyl having 1 to 8 carbon atoms or cyclohexyl.

6. The method according to claim 1, wherein $R_1$ and $R_2$ are different and are each hydrogen or a straight or branched alkyl having 1 to 3 carbon atoms; $R_3$ and $R_6$ are the same or different and are each a straight or branched alkyl having 1 to 3 carbon atoms or cyclohexyl; and $R_4$ and $R_5$ are the same or different and are each hydrogen or a straight or branched alkyl having 1 to 3 carbon atoms.

7. The method according to claim 1, wherein $R_1$ and $R_4$ are propyl; $R_2$ and $R_5$ are hydrogen; and $R_3$ and $R_6$ are the same or different and are each a straight or branched alkyl having 1 to 3 carbon atoms or cyclohexyl.

8. The method according to claim 1, wherein $R_1$ and $R_2$ are different and are each hydrogen or an alkyl having 1 to 3 carbon atoms; $R_3$ is an alkyl having 1 to 3 carbon atoms or cyclohexyl; X is the group;

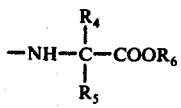

wherein $R_4$ and $R_5$ are the same or different and are each hydrogen or an alkyl having 1 to 3 carbon atoms, $R_6$ is an alkyl having 1 to 3 carbon atoms or cyclohexyl; and Y is the group:

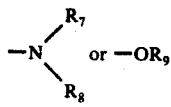

wherein $R_7$, $R_8$ and $R_9$ are the same or different and are each hydrogen, an alkyl having 2 to 8 carbon atoms or cyclohexyl.

9. The method according to claim 1, wherein $R_1$ and $R_4$ are propyl; $R_2$ and $R_5$ are hydrogen; $R_3$ and $R_6$ are propyl; $R_7$ is octyl or cyclohexyl; $R_8$ is hydrogen; and $R_9$ is ethyl.

10. The method according to claim 1, wherein said s-triazine derivative has the formula

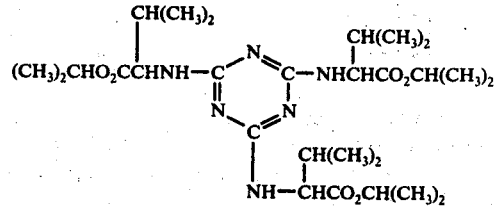

11. The method according to claim 1, wherein said s-triazine derivative has the formula:

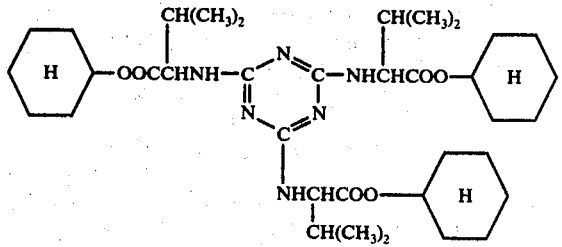

* * * * *

UNITED STATES PATENT AND TRADEMARK OFFICE
CERTIFICATE OF CORRECTION

PATENT NO. : 4,104,040
DATED : August 1, 1978
INVENTOR(S) : Naobumi OI et al

It is certified that error appears in the above-identified patent and that said Letters Patent are hereby corrected as shown below:

IN THE HEADING OF THE PATENT:

Please add the following:

-- [30]   Foreign Application Priority Data

Feb. 26, 1975 [JP]   Japan ................... 50-24335

Signed and Sealed this

Twentieth Day of February 1979

[SEAL]

Attest:

RUTH C. MASON
Attesting Officer

DONALD W. BANNER
Commissioner of Patents and Trademarks